(12) United States Patent
Thistle

(10) Patent No.: US 10,932,809 B2
(45) Date of Patent: Mar. 2, 2021

(54) TISSUE SHAVING DEVICE HAVING A FLUID REMOVAL PATH

(71) Applicant: Medos International Sàrl, Le Locle (CH)

(72) Inventor: Robert C. Thistle, Bridgewater, MA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 369 days.

(21) Appl. No.: 15/625,278

(22) Filed: Jun. 16, 2017

(65) Prior Publication Data

US 2017/0281197 A1    Oct. 5, 2017

Related U.S. Application Data

(63) Continuation of application No. 14/103,200, filed on Dec. 11, 2013, now Pat. No. 9,782,193.

(51) Int. Cl.
*A61B 17/3203*    (2006.01)
*A61B 17/16*    (2006.01)
(Continued)

(52) U.S. Cl.
CPC ...... *A61B 17/3203* (2013.01); *A61B 17/1622* (2013.01); *A61B 17/32002* (2013.01);
(Continued)

(58) Field of Classification Search
CPC .................. A61B 17/32002; A61B 17/3203
See application file for complete search history.

(56) References Cited

U.S. PATENT DOCUMENTS 4,184,256 A    1/1980  Loge et al.
4,649,919 A    3/1987  Thimsen et al.
(Continued)

FOREIGN PATENT DOCUMENTS

DE    10 2010 050352 A1    5/2012
JP    H0450013 U    4/1992
(Continued)

OTHER PUBLICATIONS

European Search Report for Application No. 14197213.3, dated Mar. 23, 2015. (9 pages).
(Continued)

*Primary Examiner* — Shaun L David

(57) ABSTRACT

A handle assembly for use in conjunction with a surgical cutting device is provided. The handle assembly can generally include two, detachable pieces or housings. The first housing can include electrical and mechanical components for driving a cutting assembly, such as a motor, while the second housing can include a fluid flow path that allows fluid to flow from the surgical site to a location outside of the cutting device. At least a portion of the fluid flow path can extend substantially adjacent to at least a portion of one or more components used to drive the cutting assembly to help manage the heat output of the components. The fluid flow path allows the fluid to exit the device without coming into contact with components like a motor, while also helping to cool the handle assembly. Systems and methods for cutting tissue are also provided.

20 Claims, 6 Drawing Sheets

(51) Int. Cl.
*A61B 17/32* (2006.01)
*A61B 17/00* (2006.01)
*A61B 17/29* (2006.01)
*A61B 90/00* (2016.01)

(52) U.S. Cl.
CPC ............ *A61B 2017/0023* (2013.01); *A61B 2017/0046* (2013.01); *A61B 2017/00477* (2013.01); *A61B 2017/2948* (2013.01); *A61B 2090/0813* (2016.02); *A61B 2217/005* (2013.01)

(56) References Cited

U.S. PATENT DOCUMENTS

| | | |
|---|---|---|
| 5,084,052 A | 1/1992 | Jacobs |
| 5,275,609 A | 1/1994 | Pingleton et al. |
| 5,490,860 A | 2/1996 | Middle et al. |
| 5,529,580 A | 6/1996 | Kusunoki et al. |
| 5,569,284 A | 10/1996 | Young et al. |
| 5,810,809 A | 9/1998 | Rydell |
| 5,871,493 A | 2/1999 | Sjostrom et al. |
| 5,906,629 A | 5/1999 | Oren et al. |
| 6,152,941 A | 11/2000 | Himes et al. |
| 6,171,300 B1 | 1/2001 | Adams |
| 6,312,441 B1 | 11/2001 | Deng |
| 6,635,067 B2 | 10/2003 | Norman |
| 7,237,990 B2 | 7/2007 | Deng |
| 7,458,940 B2 | 12/2008 | Miller |
| 7,510,563 B2 | 3/2009 | Cesarini et al. |
| 7,654,321 B2 | 2/2010 | Zazovsky et al. |
| 7,658,755 B2 | 2/2010 | Machold et al. |
| 7,922,737 B1 | 4/2011 | Cesarini et al. |
| 9,782,193 B2 | 10/2017 | Thistle |
| 2002/0040229 A1* | 4/2002 | Norman ........... A61B 17/32002 606/180 |
| 2004/0092992 A1 | 5/2004 | Adams et al. |
| 2005/0065453 A1 | 3/2005 | Shabaz et al. |
| 2005/0159677 A1 | 7/2005 | Shabaz et al. |
| 2008/0208233 A1 | 8/2008 | Barnes et al. |
| 2008/0243029 A1 | 10/2008 | Howard et al. |
| 2012/0022526 A1 | 1/2012 | Aldridge et al. |
| 2012/0123203 A1* | 5/2012 | Riva ................. A61B 1/018 600/104 |
| 2012/0130165 A1 | 5/2012 | Riva |
| 2013/0060272 A1 | 3/2013 | Thistle |
| 2014/0155889 A1 | 6/2014 | Edwards et al. |
| 2014/0155897 A1 | 6/2014 | Heiny et al. |
| 2014/0155925 A1 | 6/2014 | Riva |
| 2015/0157352 A1 | 6/2015 | Thistle |

FOREIGN PATENT DOCUMENTS

| | | |
|---|---|---|
| WO | 94/18894 A1 | 9/1994 |
| WO | 2008/080148 A2 | 7/2008 |
| WO | 2010/146432 A1 | 12/2010 |
| WO | 2012/059228 A1 | 5/2012 |
| WO | 2012/176034 A1 | 12/2012 |

OTHER PUBLICATIONS

Japanese Office Action for Application No. 2014-249799, dated Sep. 18, 2018 (7 pages).

\* cited by examiner

TISSUE SHAVING DEVICE HAVING A FLUID REMOVAL PATH

CROSS REFERENCE TO RELATED APPLICATION

The present application claims priority to and is a continuation of U.S. application Ser. No. 14/103,200, filed Dec. 11, 2013, and entitled "Tissue Shaving Device Having a Fluid Removal Path," which is hereby incorporated by reference in its entirety.

FIELD

The present invention relates to endoscopic shavers for cutting and removing tissue from the body and methods of using the same.

BACKGROUND

Arthroscopy is a minimally invasive surgical technique commonly used for removing diseased or damaged tissue from intra-articular regions of the body, such as the shoulder, hip, wrist, knee, and spine. Arthroscopic shavers can be used to remove bone, cartilage, and other soft tissue from a patient's joint with less surgical trauma to the joint than conventional surgical techniques. Typically, an arthroscopic shaver is an electro-mechanical device that includes a handpiece and a cutting assembly. The cutting assembly often has an elongate, rotatable member for cutting tissue and removing tissue and fluid from a surgical site. The handpiece usually has an integrated aspiration/suction port for transferring tissue and fluid through the handpiece and to a waste collection container. The handpiece can be releasably mated to the cutting assembly so that the cutting assembly can be disposed of after each use.

During an arthroscopic procedure, the cutting assembly of the shaver is inserted into a small incision. Suction is applied to a suction port that extends through the handpiece, causing bodily tissue and associated fluids to flow through the cutting assembly and out through a proximal end of the handpiece. After the procedure is completed, the shaver blade is typically disposed of while the handpiece is sent to a processing center for cleaning and sterilization. Because fluid and tissue can become lodged inside of the handpiece, the handpiece must be thoroughly cleaned after each use through an aggressive series of brushing operations and/or using automated washing machines. Although the brushing is necessary to remove biological material from the handpiece, it can decrease the durability of the mechanical components and damage the seals within the shaver handpiece. There is also evidence that these conventional cleaning techniques are ineffective at removing biological material. The United States Food and Drug Administration has investigated the cleaning of shaver handpieces and found numerous cases where tissue has remained in the shavers after cleaning, compromising the sterility of a surgical site.

A further problem with current tissue shavers is that during an arthroscopic procedure they have a tendency to generate a substantial amount of heat. This is because the amount of power used to operate the shaver can be significant. For example, a motor inside of a handpiece of a shaver can require 50 or more watts of power to operate. When a shaver generates a substantial amount of heat, it can be difficult or otherwise uncomfortable for the user to hold the shaver handpiece in his or her hand. Furthermore, the performance of the shaver can be negatively impacted due to overheating.

Accordingly, there remains a need for a tissue shaver that is easier to clean, has a decreased risk of contaminating a surgical site, and that reduces or otherwise counteracts the amount of heat generated by the device.

SUMMARY

Devices, systems, and methods are generally provided for cutting and removing tissue during a surgical procedure. In one exemplary embodiment, a surgical cutting device includes a cutting assembly and a handpiece assembly. The cutting assembly generally includes components that cut the tissue, including a cutting tool and at least one shaft to rotate the cutting tool. Driver components, such as a driver or motor and a drive shaft, can be used to rotate the at least one shaft, and thus the cutting tool, and can be disposed in the handpiece assembly. The handpiece assembly can generally be made of two housings or assemblies. The first housing, sometimes referred to as a driver assembly, can include a fluid impervious housing that encloses a motor. The second housing, sometimes referred to as a shaver assembly, can have a handle portion and a fluid flow path disposed in the shaver assembly. A distal end of the driver assembly can be removably matable with and at least partially enclosed within a proximal portion of the handle portion of the shaver assembly. At least one shaft of the cutting assembly can extend distally from the shaver assembly, and at least one shaft can include a cutting tool located on its distal end. A lumen can extend substantially through at least one of the shafts and can be in fluid communication with the cutting tool. The fluid flow path can extend through the lumen of the shaft to a conduit at a proximal end of the handle portion. Further, the fluid flow path can have a reservoir portion that is intermediate the conduit and the shaft lumen such that the reservoir portion extends substantially adjacent to at least a portion of the driver assembly.

In some embodiments, a distal portion of the fluid flow path can extend substantially parallel to a longitudinal axis extending through the shaft having a lumen, and a proximal portion of the fluid path can extend away from the longitudinal axis at an angle that is acute with respect to the longitudinal axis at a proximal end of the handle portion. The driver assembly can be removably attachable to the shaver assembly such that the driver assembly is reusable and the shaver assembly is disposable. A seal can be disposed between the shaver assembly and the driver assembly.

A hub assembly can be associated with the shaver assembly. For example, a hub assembly can be coupled to the at least one shaft and can be in mechanical communication with the motor such that operation of the motor is effective to rotate at least a portion of the hub assembly and the at least one shaft. A second seal, located distal of a first seal disposed between the shaver and driver assemblies, can be configured to form a seal around the hub assembly. In some embodiments, the first and second seals can be coupled to each other.

Another exemplary embodiment of a surgical cutting device includes a first housing and a second housing. The first housing can have at least one shaft extending distally from it, and a cutting tool can be disposed on a distal end of at least one of the shafts. The first housing can also have a fluid flow path extending through it. The fluid flow path can be in fluid communication with a lumen disposed in at least one of the shafts. The second housing can include a fluid impervious outer wall that encloses a motor. A distal portion of the second housing can be removably coupled within a portion of the first housing such that the outer wall of the second housing is proximate to the fluid flow path of the first housing.

In some embodiments, the fluid flow path can include a reservoir portion disposed substantially adjacent to at least a portion of the motor. A distal portion of the fluid flow path can extend substantially parallel to a longitudinal axis that extends through the shaft having the lumen disposed therein, while a proximal portion of the fluid flow path can extend away from the longitudinal axis at an angle that is acute with respect to the longitudinal axis at a proximal end of the device.

The first housing can include an elongate, elliptical opening that is configured to receive the second housing. The opening can form an angle with a longitudinal axis that extends through the shaft having a lumen disposed therein. The angle formed between the opening and the longitudinal axis can be in the range of about 30 degrees to about 60 degrees. In some embodiments, the first housing can include a mating feature at its proximal end. The mating feature can be configured to mate with a complementary mating feature located at a proximal end of the second housing. The configuration of the first and second housings can be such that when the first and second housings are detached from each other, any lumen formed in each of the first and second housings is exposed to an outside environment. This can ease a cleaning and sterilization process by exposing all openings in which fluid and tissue can be trapped by simply detaching the first housing from the second housing.

A first seal can be disposed between the first and second housings. Further, a second seal can be coupled to the first seal and can be configured to form a fluid tight seal around a hub assembly associated with the second housing. The hub assembly can include, for example, both an outer hub and an inner hub. The outer hub can be coupled to the first housing and to an outer shaft of the at least one shaft, and the outer shaft can have a lumen extending through it. The inner hub can be coupled to the outer hub and can be releasably mated to an inner shaft of the at least one shaft. The inner shaft can be disposed in the lumen of the outer shaft, and itself can include a lumen extending therethrough. The inner shaft can also have an exit port that is in fluid communication with the fluid flow path. The inner hub can be configured to releasably mate with a complementary mating feature on a driver assembly disposed in the second housing. Operation of the driver assembly by the motor can be effective to rotate the inner hub, and thus the shaft coupled to the inner hub.

One exemplary embodiment of a method of cutting tissue includes operating a surgical cutting device to cut tissue at a surgical site. The device can have a first housing and a second housing that are removably coupled to each other, with the first housing having at least one shaft extending distally from it and a cutting tool disposed on a distal end of at least one of the shafts. The device can further include a fluid flow path extending through the first housing and being in fluid communication with a lumen extending through at least one of the shafts. The second housing can have a motor disposed in it. The exemplary method can include applying a suction force through the fluid flow path to move fluid and tissue away from the surgical site and toward a proximal end of the cutting device such that the passage of fluid through the fluid flow path is adjacent to the motor enclosed within the second housing. As a result, the motor can be effectively cooled. The method can further include detaching the first housing from the second housing. In some embodiments, the first housing can be discarded following a surgical procedure. The second housing, meanwhile, can be reusable. Accordingly, the method can further include cleaning and sterilizing the second housing for reuse.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, to the extent that a component is described using a numerical reference, e.g., "first housing" or "second housing," such reference does not have any significance, and thus it in no way indicates any particular order, placement, location, etc. of the component with respect to any other component, object, step, etc. In fact, such numerical references can be used interchangeably. For instance, a component described in the specification as a "first housing" can be recited in the claims as a "second housing." A person skilled in the art would be able to understand such interchangeable usage.

Figure 1:
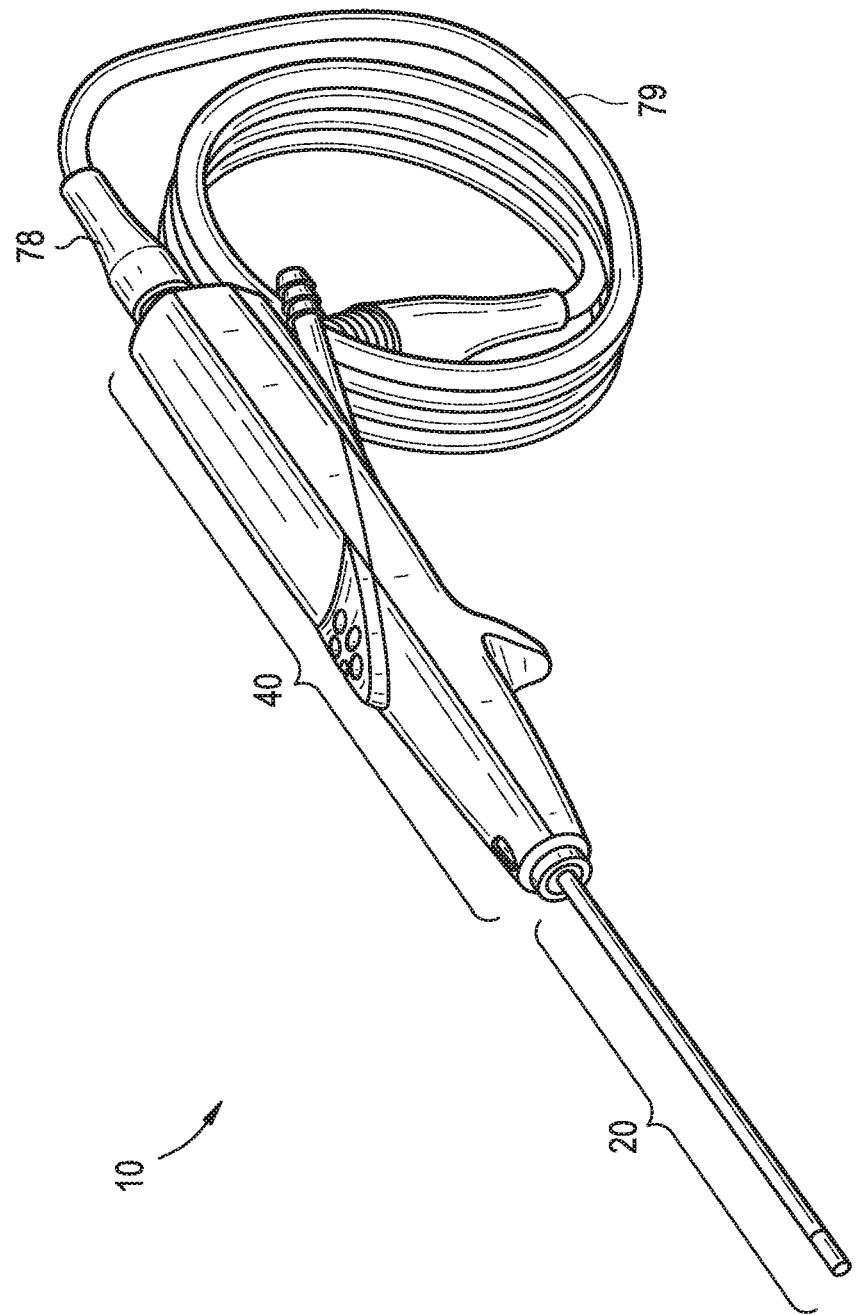
FIG. 1 is a perspective view of one exemplary embodiment of a tissue shaver.

The present disclosure provides for a tissue shaver that is configured to divert fluid and tissue away from a surgical site and use that fluid to help manage the heat produced by driver components that operate the shaver, such as a motor, without allowing the fluid and tissue to contact such driver components. One exemplary embodiment of a tissue shaver in accordance with the present disclosure is provided for in FIG. 1. In general, an arthroscopic shaver 10 is provided for removing tissue and reshaping a patient's anatomy, and can include a cutting assembly 20 for cutting tissue and a handpiece assembly 40 for operating the cutting assembly 20. Driver components, such as a motor (not shown), can be disposed in the handpiece assembly to also assist in operating the cutting assembly 20. Power can be provided to the shaver 10 in a variety of ways, some of which are described further below, and in the illustrated embodiment power is supplied through an electrical wire 79 connected to a socket 78 that extends proximally from the handpiece assembly 40.

Figure 2:
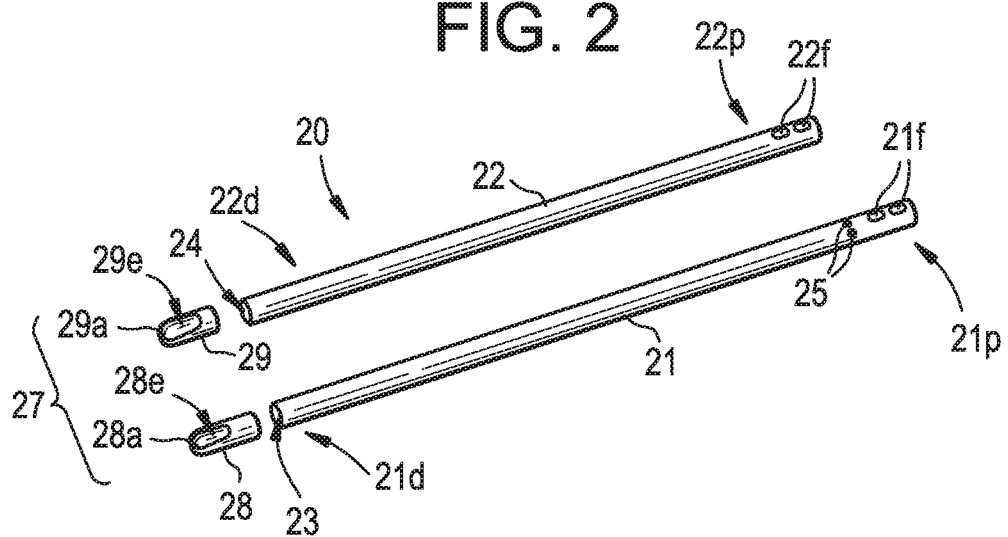
FIG. 2 is a perspective view of inner and outer shafts of a cutting assembly of the tissue shaver of FIG. 1.

The cutting assembly 20 can generally include one or more elongate shafts having one or more cutting tools disposed at a distal end thereof, and a lumen extending through at least one of the shafts to allow fluid and tissue to pass therethrough. In the illustrated embodiment provided in FIG. 2, an elongate inner shaft 21 is configured to be disposed within an elongate outer shaft 22, and the two shafts 21, 22 operate together to cut tissue using cutting members 28, 29 disposed thereon. Generally, the inner shaft 21 can have a length that is greater than a length of the outer shaft 22 because the inner shaft 21 extends further into the handpiece assembly 40, and the inner shaft 21 can have an outer diameter that is less than an inner diameter of the outer shaft 22 so that it can rotate within the outer shaft 22. The outer shaft 22 can include a lumen 24 extending therethrough to at least receive the inner shaft 21, and the inner shaft 21 can include a lumen 23 extending therethrough to allow fluid and tissue to pass therethrough.

Both shafts 21, 22 can include features that are configured to fixedly secure the shafts in a hub assembly (not shown). As shown, each shaft 21, 22 can include a plurality of friction elements 21f, 22f, which can be used to form a press-fit between the shafts 21, 22 and respective hubs of the hub assembly, as described in further detail below. Further, the inner shaft 21 can include one or more ports 25 for transferring tissue and fluid from the inner shaft 21 to an exit port of the hub assembly, as also described further below with respect to FIG. 10. The port(s) 25 are preferably positioned at a location proximal to the proximal end 22p of the outer shaft 22 when the device 10 is assembled so that the outer shaft 22 does not block fluid flow through the port(s) 25.

A cutting tool 27 for excising tissue from a surgical site can be formed by inner and outer cutting members 28, 29 disposed at distal ends 21d, 22d of the inner and outer shafts 21, 22, respectively. While the cutting members 28, 29 can have a variety of configurations, in one embodiment they are configured to excise adjacent tissue from a surgical site. In the illustrated embodiment, the cutting members 28, 29 have a substantially cylindrical shape and include elliptical shaped openings 28e, 29e that extend through an outer sidewall of the members 28, 29. The openings 28e, 29e can have serrated teeth 28a, 29a on their circumferences for cutting tissue. In the illustrated embodiment, the cutting members 28, 29 are over-molded onto their respective shafts 21, 22, although any other number of mating techniques known to those skilled in the art can be used.

The cutting assembly 20 can be operated by components included as part of the handpiece assembly 40, such as drivers and actuators. The handpiece assembly 40 can preferably be configured to facilitate grasping the device 10 and to allow device operation with one hand. In exemplary embodiments provided for herein, including as shown in FIG. 3, the handpiece assembly 40 includes two components or housings 60, 80 that are removably matable with each other.

Figure 3:
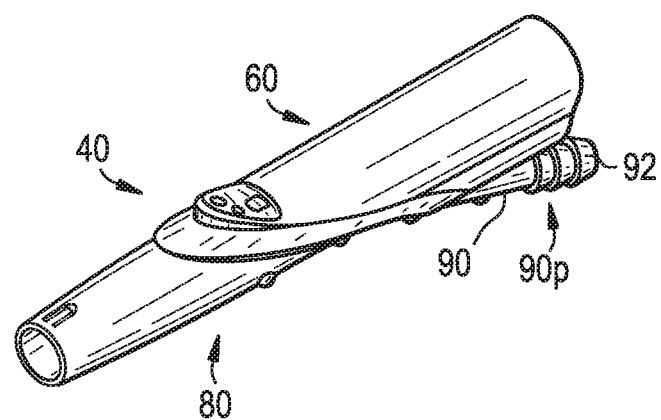
FIG. 3 is a perspective view of a handle assembly of the tissue shaver of FIG. 1.

The first housing 60 can include driver components 70 (shown in FIG. 5B), such as a motor and a drive shaft, for operating the cutting assembly 20 (not shown in FIG. 3). At least a portion of some of the components can be disposed within a fluid impervious wall or chamber of the housing 60 to prevent fluid and tissue from interfering with their operation. Examples of driver components and configurations related to the same are discussed in greater detail below. Generally, however, the driver components 70 can be in mechanical cooperation with components of the cutting assembly 20, e.g., the elongate shafts 21, 22 and the cutting members 28, 29, such that actuation of the driver components 70 rotates the shafts 21, 22 and allows the cutting members 28, 29 to cut tissue.

The second housing 80 can provide a fluid flow path 90 having a distal end 90d (shown in FIG. 7B) that is in fluid communication with the lumen 23 of the inner elongate shaft 21 and a proximal end 90p that has a conduit 92. As a result, fluid can flow between the cutting tool 27 and the conduit 92 by traveling through the lumen 23 and the fluid flow path 90. The fluid flow path 90 formed in the second housing 80 can extend substantially adjacent to at least a portion of the driver components 70 located in the first housing 60, including a motor, such that fluid traveling therethrough can help to cool the driver components 70 (shown in FIG. 5B) as they heat up during operation. Further details about both housings 60, 80, and the fluid flow path 90, are provided below.

Figure 4:
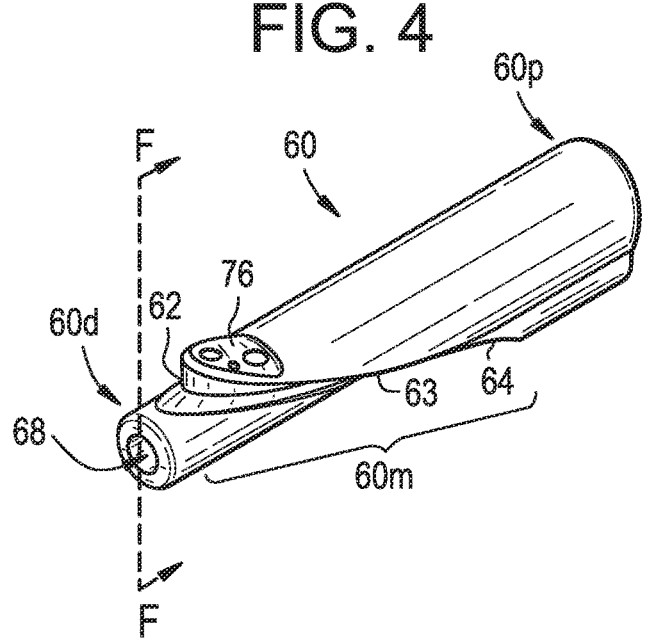
FIG. 4 is a perspective view of a first housing of the handle assembly of FIG. 3.
Figure 5A:
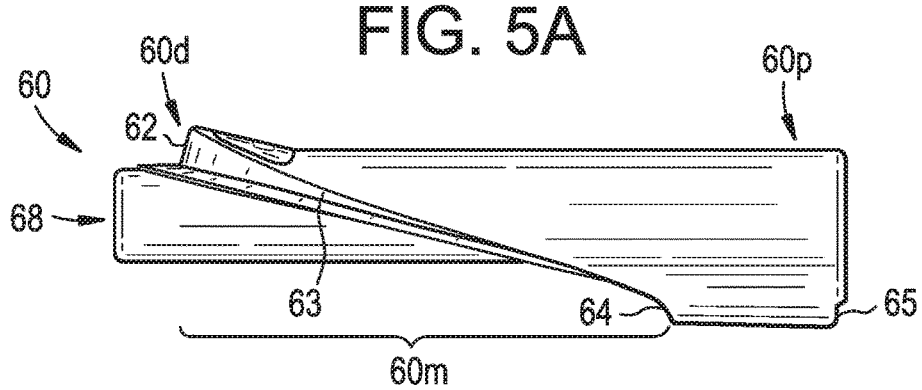
FIG. 5A is a side view of the first housing of FIG. 4.
Figure 5B:
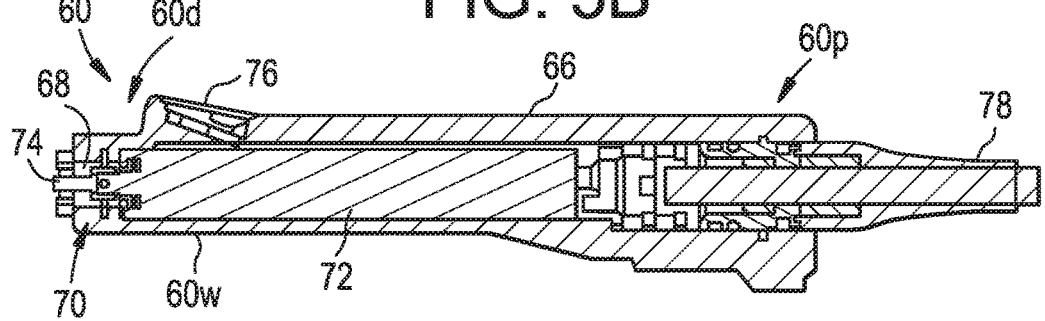
FIG. 5B is a side cross-sectional view of the first housing of FIG. 4 taken across the line F-F and having driver components disposed therein.
Figure 6:
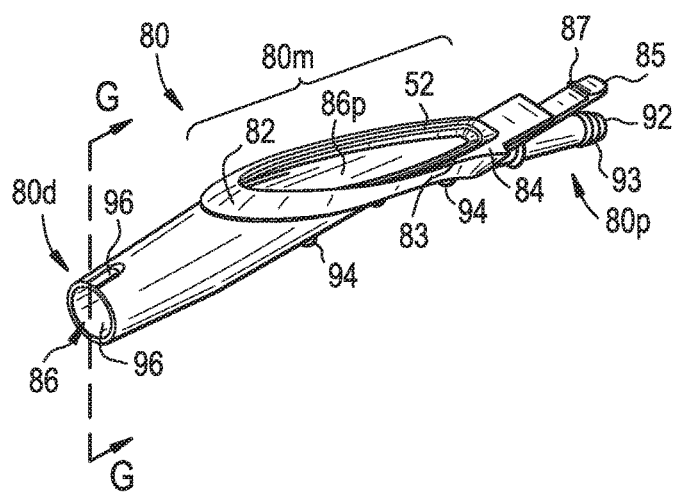
FIG. 6 is a perspective view of a second housing and an o-ring assembly of the handle assembly of FIG. 3.
Figure 7A:
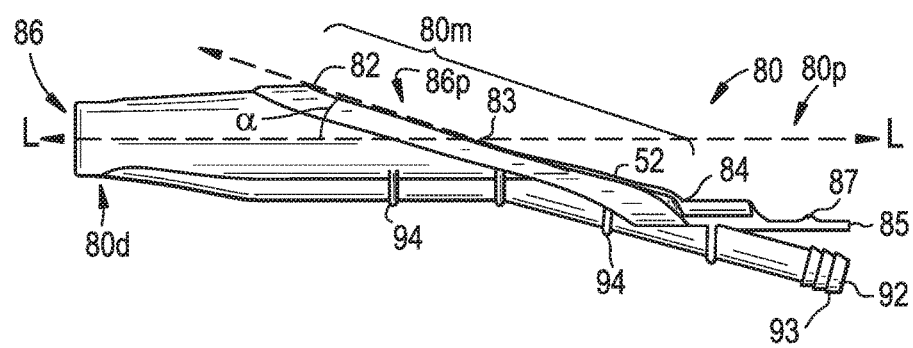
FIG. 7A is a side view of the second housing and the o-ring assembly of FIG. 6.

FIGS. 4, 5A, and 5B illustrate the first housing 60, which is the portion of the handpiece assembly 40 configured to house driver components for operating the cutting assembly 20. While the first housing 60 can have a variety of configurations, in the illustrated embodiment the first housing 60 has a generally cylindrical shape having a mating end 60m that is complementary in shape to a mating end 80m of the second housing 80 (FIGS. 6 and 7A). As shown in FIG. 5A, the mating end 60m can include a top mating surface 62, a bottom mating surface 64, and an elliptical mating surface 63 that extends between the top and bottom mating surfaces 62, 64, each of which can be configured to engage complementary surfaces of the second housing 80 and/or surfaces of a seal, such as an o-ring, disposed between the two housings 60, 80. The first housing 60 can also include a catch portion 65 configured to be engaged by a complementary deflectable tab 85 (FIGS. 6, 7A, and 7B) of the second housing 80 to help secure the location of the second housing 80 with respect to the first housing 60.

Driver components 70 can be disposed in the housing 60 such that at least some components, for instance a motor 72, are located in a chamber 66 of the housing 60 that is impervious to fluid. The chamber 66 can be defined by walls within the first housing 60, including an outer wall 60w that extends adjacent to the second housing 80 when the two housings 60, 80 are coupled together. A lumen 68 can be disposed distal of the chamber 66 and can be sized to receive a portion of the motor 72 and a drive shaft 74 coupled thereto. In the illustrated embodiment, the lumen 68 is formed in a distal end 60d of the first housing 60. The configuration between the chamber 66 and the lumen 68 is such that fluid does not generally pass through the lumen 68 and into the chamber 66. Further, the first housing 60 can include a control panel 76 that can serve as an actuator configured to operate features of the device 10, such as the motor 72 and the components associated therewith, e.g., the drive shaft 74, elongate inner and outer shafts 21, 22, and cutting members 28, 29. Buttons on the control panel 76 can have a variety of functions. For example, each button can cause the motor 72 to operate in a different mode, such as a forward mode, a reverse mode, or an oscillating mode, or the buttons can have multiple functions depending upon the speed in which a user presses them. Additionally, in some embodiments the first housing 60 can be configured to connect to an external power source via a socket 78 that extends proximally from a proximal end 60p of the first housing 60. In alternative embodiments, the power source can be incorporated directly into the handpiece assembly 40, or other forms of powering a handheld device can be relied upon without departing from the spirit of the present disclosure.

Figure 7B:
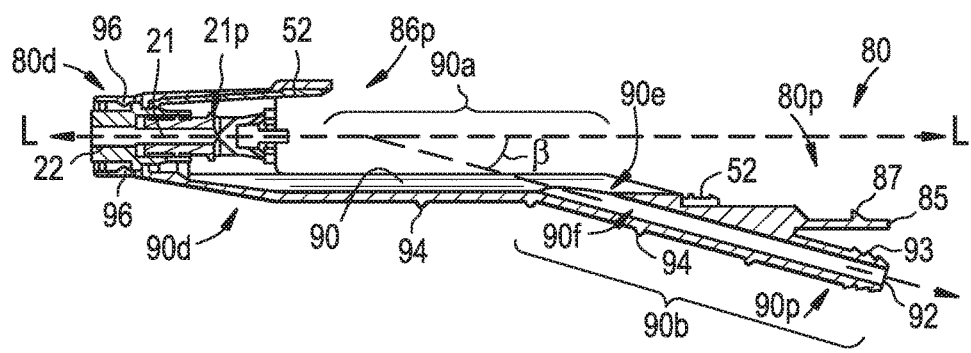
FIG. 7B is a side cross-sectional view of the second housing and o-ring assembly of FIG. 6 taken along the line G-G and having driver components disposed therein.

The second housing 80, shown in FIGS. 6, 7A, and 7B, is generally configured to both receive a portion of the first housing 60, and provide a fluid flow path 90 so that fluid and tissue can flow between the surgical site and an outside environment without contacting particular driver components 70, such as the motor 72. While the second housing 80 can have a variety of configurations, in the illustrated embodiment the second housing 80 has a generally cylindrical shape that is complementary to the cylindrical shape of the first housing 60. In particular, a mating end 80m of the second housing 80 can be complementary in shape to the mating end 60m of the first housing 60. Accordingly, a top mating surface 82 can be configured to complementarily mate with the top mating surface 62, a bottom mating surface 84 can be configured to complementarily mate with the bottom mating surface 64, and an elliptical mating surface 83 extending between the top and bottom mating surfaces 82, 84 can be configured to complementarily mate with the elliptical mating surface 63. In the illustrated embodiment, an o-ring 52 is disposed between the mating surfaces 60m, 80m. The o-ring 52 can help to provide a seal between the two housings 60, 80 of the handpiece assembly 40, and thus does not generally impact the complementary engagement between the mating surfaces 60m, 80m. Additional features of the o-ring 52 are provided further below.

The second housing 80 can also include a lumen 86 extending through a portion thereof and configured to receive the distal end 60d of the first housing 60. As shown, a proximal end 86p of the lumen 86 can be defined by the elliptical mating surface 83, thus forming an elongate, elliptical opening. The elongate elliptical opening can form an acute angle α with a longitudinal axis L extending through the device 10. The acute angle α can be in the range of about 15 degrees to about 90 degrees, more specifically in the range of about 30 degrees to about 60 degrees, and in one exemplary embodiment the angle α is about 30 degrees. In some embodiments, the proximal end 86p of the lumen 86 can be approximately perpendicular to the longitudinal axis L and can receive a portion of the first housing 60 therein. A person skilled in the art will recognize a variety of other configurations that can be used to allow the second housing 80 to receive the first housing 60. A mating feature, as shown a deflectable tab 85 having an engagement tooth 87, can be provided at a proximal end 80p of the second housing 80. The tooth 87 can engage the catch portion 65 to form a snap-fit between the first and second housings 60, 80. A person skilled in the art will recognize other mating features, and other locations for mating features, that can be used in conjunction with the first and second housings 60, 80 to help maintain a location of one housing with respect to the other.

A fluid flow path 90 can extend through at least a portion of the second housing 80. As shown in FIG. 7B, the path 90 can extend from a distal end 80d of the second housing 80 to a proximal end 80p of the second housing 80, with a distal end 90d of the path 90 being proximate to a proximal end 21p of the inner shaft 21, and a proximate end 90p of the path 90 being located at a conduit 92. The conduit 92 can having mating features 93 that can be used to assist in coupling another device to the tissue shaver 10, such as a pump and hose to supply fluid to the surgical site or a vacuum source to supply a vacuum force to the surgical site to extract fluid and/or tissue. In some embodiments, a valve (not shown) can be provided to help control the flow of fluid through the fluid flow path 90. For example, when a vacuum source is hooked up to the conduit 92, a button on the control panel 76 can operate the valve to selectively apply suction through the fluid flow path 90. Alternatively, suction can be applied and controlled using a separate device. Still further, the handpiece assembly 40 as a whole can integrated with a fluid management system, such as the FMS Duo®+ of DePuy Mitek, Inc., 325 Paramount Drive, Raynham, Mass. 02767.

In between the two ends 90d, 90p of the path 90, at least a portion thereof can be configured to extend substantially adjacent to at least a portion of the driver components 70, such as the motor 72. A distal, reservoir portion 90a of the path 90 can extend substantially parallel to the longitudinal axis L and can be disposed directly adjacent to the outer wall 60w of the first housing 60, and thus the chamber 66. A more proximal, exit portion 90b of the path 90 can extend at an acute angle β to the longitudinal axis L, away from the driver components 70. The acute angle β can be in the range of about 10 degrees to about 80 degrees, more specifically in the range of about 10 degrees to about 60 degrees, and in one exemplary embodiment the angle β is about 25 degrees. In some embodiments, the exit portion 90b of the path 90 can be approximately parallel to the longitudinal axis L.

Figure 8A:
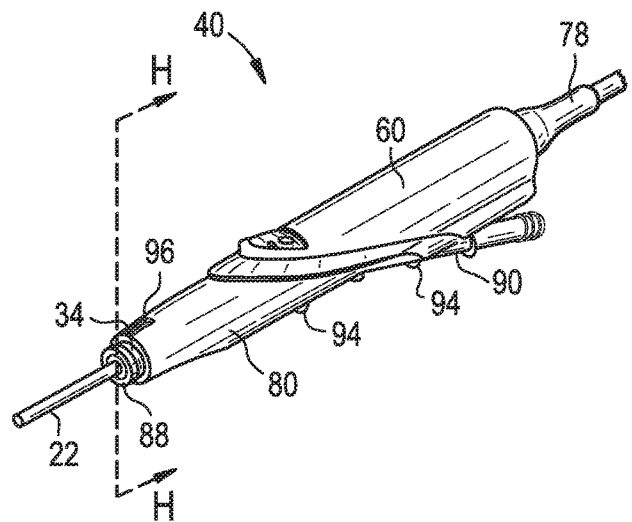
FIG. 8A is a perspective view of the handle assembly of FIG. 3, the handle assembly being associated with two elongate shafts and a socket.
Figure 8B:
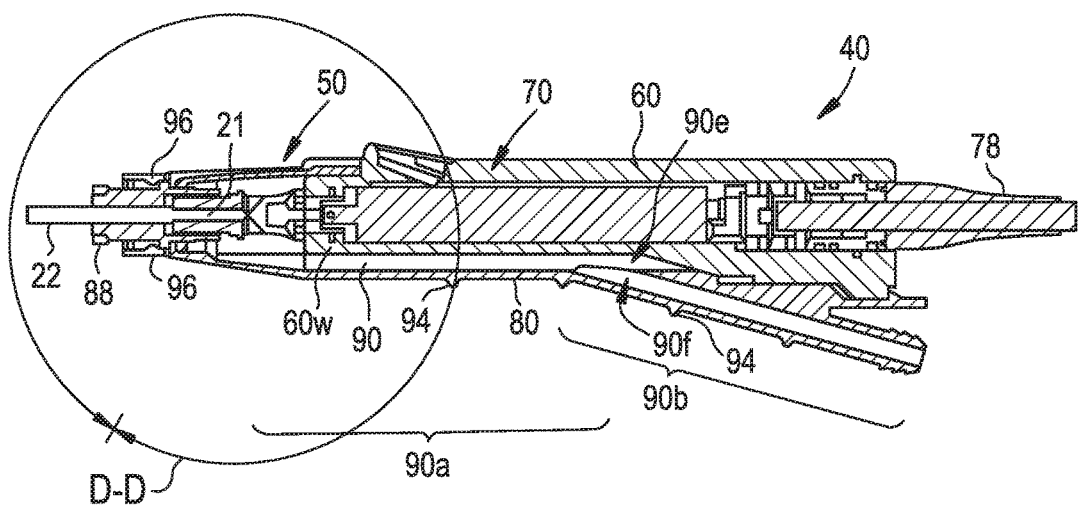
FIG. 8B is a side cross-sectional view of the handle assembly of FIG. 8A taken along the line H-H and having driver components disposed therein.

As shown in FIGS. 8A and 8B, by having at least a portion of the fluid flow path 90 extend substantially adjacent to at least a portion of the driver components 70, fluid flowing through the path 90 can help to cool the handpiece assembly 40. A person skilled in the art will recognize that the configuration and location of the fluid flow path 90 with respect to the driver components illustrated herein is just one configuration of a path configured to cool driver components 70 disposed in the first housing 60 without contacting the driver components 70, and that a variety of other configurations can be used to achieve the same purpose without departing from the spirit of the present disclosure. For example, although in the illustrated embodiment a portion 90e of the reservoir portion 90a extends proximally beyond a beginning 90f of the exit portion 90b, in other embodiments the fluid flow path can be a singular path with no additional portions like the portion 90e. By way of further non-limiting examples, in other embodiments the reservoir portion 90a of the fluid flow path 90 can be configured to wrap around the chamber 66 at least once before entering the exit portion 90b.

The second housing 80 can include additional features to assist a user in operating the device. For example, one or more surface features 94 can be formed on the second housing 80 to provide friction between a user's hand and the handpiece assembly 40. Such features can also be provided for on the first housing 60. Further, two detents 96 can be formed in the distal end 80d of the second housing. The detents 96 can be used to help couple driver components 70, such as a hub assembly, to the handpiece assembly 40, as described in further detail below.

Each of the first and second housings 60, 80, as well as the handpiece assembly 40 that the housings 60, 80 form when coupled together as shown in FIGS. 8A and 8B, can have a variety of configurations and shapes, depending, at least in part, on the configurations of the respective housings 60, 80, the components of the shaver 10 associated therewith, and the type of procedure with which the handpiece assembly 40 will be used. In the illustrated embodiment, the first housing 60 can be generally cylindrical in nature, while the second housing 80 can have a cylindrical portion at a distal end 80d thereof and can also include a lumen 86 having a proximal end 86p that is both substantially elliptical in shape and configured to receive a distal end 60 of the first housing 60. The resulting handpiece assembly 40 is also generally cylindrical. Each of the housings 60, 80, as well as the resulting handpiece assembly 40, can have other configurations and shapes without departing from the spirit of the present disclosure. A size of the resulting handpiece assembly 40 can be a size similar to handpieces associated with tissue shavers known to those skilled in the art.

The first and second housings 60, 80 can be formed from a variety of materials. In some instances both housings 60, 80 can be formed from similar or identical materials, while in other embodiments different materials can be used to form the housings 60, 80. In some exemplary embodiments, the first housing 60 is made from one or more conductive materials, which can help extract heat from the driver components. Some non-limiting examples of conductive materials that can be used to form the first housing 60 include titanium, aluminum, and surgical grade stainless steel. The second housing 80 can likewise be formed from one or more materials configured to help extract heat away from the driver components. In alternative embodiments, the second housing 80 can be formed from one or more materials used more often in a disposable capacity. For example, in some embodiments the second housing 80 can be formed from a polymer, such as Radel® polyphenylsulfones (PPSU), available from Solvay Specialty Polymers Americas (SpecialtyPolymers.Americas@solvay.com).

Either or both of the first and second housings 60, 80 can be reusable. The construction of the handle assembly 40 is such that when the two housings 60, 80 are separated, any holes and lumens associated therewith are easily accessible and thus capable of being cleaned and sterilized. The techniques used for cleaning and sterilizing include any of those known to those skilled in the art, although those techniques become easier due to the design of the handle assembly that allows for easy hole and lumen accessibility. Alternatively, at least one of the housings 60, 80 can be disposable. For example, in instances in which the second housing 80 is made from a polymer, it may be more advantageous to dispose of the second housing after it is used and use a new second housing with the first housing 60 rather than clean the fluid flow path 90, and any other exposed openings, prior to subsequent use. In certain aspects, the handpiece assembly 40 can be configured to be autoclaved without damaging the functionality of the motor so that the handpiece assembly 40 can be sterilized after each use.

Figure 9:
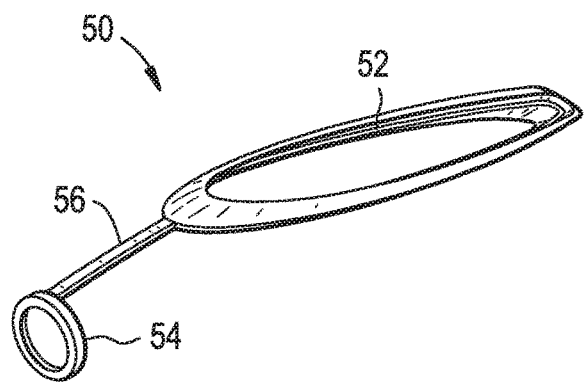
FIG. 9 is a perspective view of the o-ring assembly of FIG. 6.

Disposed within the handpiece assembly can be one or more structures for providing a seal between the first and second housings 60, 80. In the illustrated embodiment, the structure is an o-ring assembly 50, as shown in FIG. 9. The o-ring assembly 50 can include a first o-ring 52 that forms a seal between the two housings 60, 80, and a second, more distal o-ring 54 that provides a seal between the second housing 80 and driver components, in particular a portion of an outer hub 34 of a hub assembly 30. As shown, the first o-ring 52 has an elongate, elliptical shape, complementary to the shape of the proximal end 86p of the lumen 86 of the second housing 80 and the diagonal mating surface 63 of the first housing 60, while the second o-ring 54 has a more circular shape that is complementary to the shape of the portion of the outer hub 34 around which it is disposed. In some embodiments, a connector 56 can extend between the first and second o-rings 52, 54 to form a single assembly or structure 50. The o-ring assembly 50 can be a variety of other configurations and shapes, depending, at least in part, on the configurations of the first and second housings 60, 80, driver components 70, and other components of the device 10. Further, the o-ring assembly 50 can be formed from a variety of materials, including, by way of non-limiting example, an elastomer.

Figure 10:
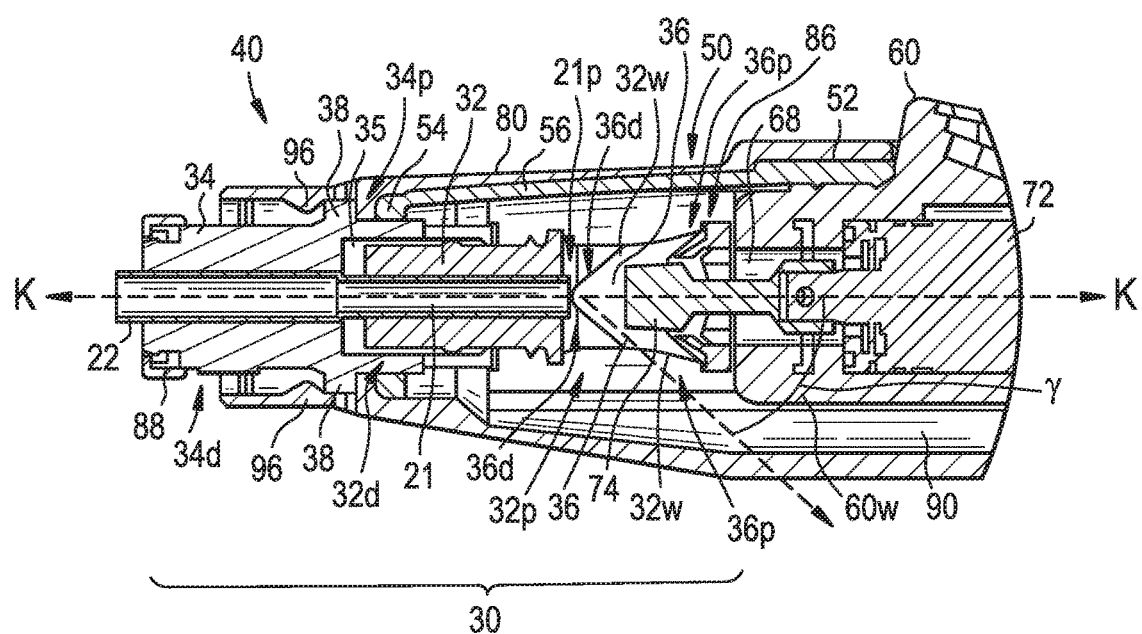
FIG. 10 is a detailed cross-sectional view of a portion of the handle assembly of FIG. 8B as identified by the circle D-D.

While the handpiece assembly 40 can be used with a variety of different cutting assemblies, driver components, and configurations of the same known to those skilled in the art, in the illustrated embodiment, as shown in FIG. 10, it is used in conjunction with driver components 70 that include the motor 72 and the drive shaft 74, and cutting assemblies 20 that include a hub assembly 30 and the elongate shafts 21, 22.

As shown, the motor 72 can be connected to the drive shaft 74 positioned in the lumen 68 of the first housing 60 and the lumen 86 of the second housing 80 and can extend toward a distal end of the handpiece assembly 40. The drive shaft 74 can be configured to mate with a variety of cutting assemblies known to those skilled in the art. In the illustrated embodiment, the cutting assembly 20 includes a hub assembly 30 and the two elongate shafts 21, 22 having cutting members 28, 29 (not shown) formed on distal ends 21d, 22d thereof. Actuation of the motor 72 can cause the drive shaft 74, and thus the hub assembly 30 and shafts 21, 22, to rotate, thereby causing the cutting members 28, 29 to cut tissue. The motor 72 can be actuated in a variety of ways, but in the illustrated embodiment, the handpiece assembly 40 is configured to connect to an external power source via the socket 78. The size and amount of power generated by the motor 72 and other driver components 70 can depend on a variety of factors, including but not limited to the size and materials used for the cutting and handpiece assemblies 20, 40, and the type of procedure with which the device 10 is being used. In some embodiments, the power output of the motor 72 can be in the range of about 20 W to about 80 W, and in one embodiment it is about 50 W. In other embodiments, the driver components can be non-electric, such as pneumatic or other driving configurations known to those skilled in the art. The design of the fluid flow path 90, and components related to the same, can be helpful to dissipate the effects of heat generated by components in such systems, including mechanical gear boxes.

The hub assembly 30 can have various configurations, but in one embodiment, as shown, the hub assembly 30 includes an outer hub 34 and an inner hub 32. While the shape of the outer hub 34 can vary, the illustrated hub 34 is generally cylindrical. The distal end 34d of the outer hub 34 can be configured to fixedly and non-rotatably mate to the outer shaft 22, and the proximal end 34p of the outer hub 34 can be configured to mate to the handpiece assembly 40 using various mating techniques, such as welding, adhesives, and mechanical engagement. As shown, tabs 38 on the proximal end 34p form a snap fit with the detents 96 of the second housing 80 so that the outer hub 34 can be removably and replaceably coupled to the handpiece assembly 40. In some embodiments, the outer shaft 22 and outer hub 34 can be integrally formed as a single component. The outer hub 34 can also include a lumen 35 that extends along a central axis K between the proximal and distal ends 34p, 34d. As shown, a more distal portion of the lumen 35 has a diameter configured to receive the outer shaft 22, while a more proximal portion of the lumen 35 has a larger diameter configured to receive the inner hub 32.

The inner hub 32 can mate to the inner shaft 21 and can rotatably couple to the outer hub 34. While the shape of the inner hub 32 can vary, the illustrated hub 32 is generally cylindrical. The inner hub 32 can have a larger diameter portion on its proximal end 32p and a smaller diameter cylindrical portion on its distal end 32d so that its proximal end 32p can mate to the handpiece assembly 40 and its distal end 32d can seat in the more proximal portion of the lumen 35 of the outer hub 34. The distal end 32d can be configured to rigidly and non-rotatably mate to the inner shaft 21, such as by a press-fit as shown, although a variety of other mating techniques can also be used. The proximal end 32p can be configured to mate with the drive shaft 74 such that actuation of the motor 72 causes rotation of the inner hub 32. Any mating technique known to those skilled in the art can be used to mate the inner hub 32 to the inner shaft 21 and the drive shaft 74, including but not limited to welding, adhesives, or mechanical engagement. In some embodiments, the inner shaft 21 and inner hub 32 can be integrally formed as a single component.

The inner hub 32 can also include one or more exit ports 36 that extend between at least one of the lumen 23 and ports 25 of the inner shaft 21 and an outer sidewall 32w of the inner hub 32. In the illustrated embodiment, two opposed exit ports 36 extend from a central location of the inner hub 32 to the outer sidewall 32w. Distal ends 36d of the exit ports 36 are in fluid communication with the inner shaft 21, and proximal ends 36p of the exit ports 36 are in fluid communication with the distal end 90d of the fluid flow path 90. Accordingly, fluid and tissue can flow from the surgical site, through the inner shaft 21, through the inner hub 32, and into the fluid flow path 90, and likewise, fluid can flow from the fluid flow path 90, through the inner hub 32, through the inner shaft 21, and to the surgical site. An angle γ of the exit ports 36 relative to the central axis K can vary, e.g., the exit ports 36 can extend perpendicular to the central axis K, parallel to the central axis K, or they can extend at an acute or obtuse angle, as shown. In some embodiments, the angle γ can be in the range of about 10 degrees to about 80 degrees, more specifically in the range of about 30 degrees to about 70 degrees, and in one exemplary embodiment the angle γ is about 60 degrees. A person skilled in the art will appreciate that the exit ports 36 can have a variety of other configurations, and can also be provided for in the outer hub 34. In a preferred embodiment, the exit port(s) 36 of the inner hub 32 is unobstructed by other components, such as the outer hub 34, so that tissue and/or fluid can flow through the exit port(s) 36. Further, each of the outer and inner hubs 34, 32 can be formed from a variety of different materials, including by way of non-limiting example, surgical grade stainless steel, titanium, and plastics.

In some embodiments, an identifier plate 88 can be associated with the cutting assembly 20 to provide information about the cutting assembly 20 to the user. For example, different colored, sized, and/or shaped identifier plates can indicate to the user a diameter of the cutting assembly associated therewith. As shown, the identifier plate 88 has a substantially cylindrical disc shape, and is coupled to the distal end 34d of the outer hub 34 by way of over-molding. Other mating techniques, including but not limited to welding, adhesives, or mechanical engagements, can also be used to associate the identifier plate 88 with the cutting assembly 20.

The components of the arthroscopic shaver can be assembled during the manufacturing process or by a user. For example, the inner shaft 21 can be mated with the inner hub 32 and the outer shaft 22 can be mated with the outer hub 34. The distal end 21d of the inner shaft 21 can be inserted into the proximal end 34p of the outer hub 34 and through the outer shaft 22 until the components are secured by a press-fit. In the alternative, the shafts 21, 22 and respective hubs 32, 34 can be integrally formed during the manufacturing process. In both embodiments, the outer and inner hubs 34, 32 can be mated to the distal end 40d of the handpiece assembly 40 by inserting the hub assembly 30 such that the tabs 38 of the outer hub 34 engage with the detents 96 of the second housing 80. Other mating techniques, including but not limited to using a free-fit, threads, or other mechanical techniques, can also be used. Further, although in the illustrated embodiment the hub assembly 30, and thus the shafts 21, 22, are coupled to the second housing 80, in other embodiments the first housing 60 can be configured to be directly coupled to the hub assembly 30 and/or the shafts 21, 22. For example, in some embodiments the first housing can include a receiving portion configured to receive one or both of the inner and outer hubs 32, 34.

In use, the cutting assembly 20 of the tissue shaver 10 can be inserted into an incision made in a patient. Optionally, the depth of the cutting assembly 20 within the incision can be monitored using fluoroscopy, X-ray, or other visualization techniques known in the art. After the cutting assembly 20 is positioned at the desired depth, suction can be applied through the fluid path 90. Tissue adjacent to the outer cutting member 29 is drawn through the openings 29e, 28e, respectively. The control panel 76 can be used to actuate the inner shaft 21 to rotate relative to the outer shaft 22. Because the shafts 21, 22 are non-rotatably coupled to the cutting members 28, 29, inner cutting member 28 rotates relative to the outer cutting member 29 and the tissue trapped in the inner cutting member 28 is cut by the serrated teeth 28a, 29a. The applied suction causes the cut tissue and/or fluid to flow through the lumen 23 in the inner shaft 21, through the ports 25 of the inner shaft 21, through the exit ports 36 of the inner hub 32, through the fluid flow path 90, and out of the conduit 92. The cut tissue and/or fluid can be collected in a suitable waste collection container. This process can be repeated until the desired amount of tissue is excised from the surgical site.

After the procedure is complete, the cutting assembly 20 can be disengaged from the handpiece assembly 40, and the second housing 80 can be disengaged from the first housing 60. Separating the first and second housings 60, 80 can expose each of the openings in the handpiece assembly 40 through which fluid can and tissue can enter, thereby allowing each opening to be cleaned so each of the two housings 60, 80 can be easily cleaned, sterilized, and reused. Alternatively, the second housing 80 can be disposed of and one or both of the first housing 60 and the cutting assembly 20 can be cleaned, sterilized, and reused.

As will be appreciated by a person skilled in the art, the tissue shavers provided can be used to remove tissue from various regions in the body, including by way of non-limiting example, shoulder, hip, wrist, knee, and spine. Likewise, as will also be appreciated by a person skilled in the art, the disclosures pertaining to the handpiece assembly 40 provided for herein can be used with many other configurations of cutting assemblies, driver components, and other related assemblies and components, including those configurations disclosed in U.S. Patent Application Publication No. 2013/0060272, entitled "Tissue Shavers," the content of which is incorporated by reference herein in its entirety. In fact, the handpiece assembly 40 is in no way limited to use only in conjunction with cutting assemblies and tissue shaving procedures. A person skilled in the art would be able to use the handpiece assembly 40 described herein with many types of instruments and tools, surgical or otherwise, to help both manage the flow of fluid through the instruments and tools, and to manage heat output by the instruments and tools to provide a cooling effect.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical cutting device, comprising:
at least one shaft having a proximal end and a distal end with a lumen formed therebetween;
a first housing coupled to the proximal end of a shaft of the at least one shaft such that the shaft extends distally therefrom;
a receiving portion configured to receive a cutting tool disposed on the distal end of the shaft, the lumen being in fluid communication with the cutting tool;
one or more ports disposed on the proximal end of the shaft, the one or more ports being in fluid communication with the lumen, and disposed distal to a proximal-most end of the shaft;
a fluid flow path extending through the first housing from the lumen of the shaft to a conduit at a proximal end of the first housing, the fluid flow path being in communication with the cutting tool through at least one port of the one or more ports; and
a second housing that encloses a motor, the second housing having a distal end that is removably matable with a proximal portion of the first housing such that at least a portion of the second housing is configured to be received within an opening in the first housing.

2. The device of claim 1, wherein the shaft is disposed in a lumen of a second shaft of the at least one shaft, the shaft having an outer diameter that is less than an inner diameter of the second shaft.

3. The device of claim 1, wherein the removable connection between the first housing and the second housing is such that when the first and second housings are detached from each other, any lumen formed in each of the first and second housings is exposed to an outside environment.

4. The device of claim 1, further comprising:
a hub assembly;
a first seal disposed between the first and second housings; and
a second seal, coupled to the first seal, and configured to form a fluid tight seal around the hub assembly when associated with the second housing.

5. The device of claim 4, wherein the hub assembly further comprises:
an outer hub configured to mate with the first housing, the outer hub being coupled to a second shaft of the at least one shaft, the shaft having an outer diameter that is less than an inner diameter of the second shaft; and
an inner hub rotatably coupled to the outer hub, the inner hub being coupled to the shaft, the shaft having a lumen extending therethrough and an exit port in fluid communication with the fluid flow path,
wherein the inner hub is configured to releasably mate with a complementary mating feature on a driver assembly disposed in the second housing,
wherein operation of the driver assembly by the motor is effective to rotate the inner hub to move the shaft coupled to the inner hub, and
wherein the inner hub is in fluid communication with one or more of the ports.

6. The device of claim 5, wherein the one or more of the ports is in fluid communication with the exit port to allow fluid and tissue to flow therethrough.

7. The device of claim 1, wherein at least one port of the one or more ports is located proximal to a location of the cutting tool.

8. The device of claim 1, wherein the one or more ports are positioned at a location along the first shaft that is proximal to an outer shaft of the at least one shafts.

9. The device of claim 1, wherein the fluid flow path includes a reservoir portion disposed adjacent to at least a portion of the motor such that fluid traveling through the reservoir portion helps cool the motor.

10. A surgical cutting device, comprising:
a cutting assembly for cutting and removing tissue;
a first housing having driver components for operating the cutting assembly, the driver components being in mechanical cooperation with the cutting assembly such that actuation of the cutting assembly allows the cutting assembly to cut and remove tissue; and
a second housing configured to mate to the first housing, the second housing having a lumen that defines a central longitudinal axis that extends through a portion thereof, the lumen being configured to receive a distal end of the first housing,
wherein the first housing includes a control panel that operates the driver components to actuate the cutting assembly, the control panel being contained separate from the second housing when the first housing is mated to the second housing, and positioned external to the second housing such that the control panel is exposed to the external environment when the first housing is mated to the second housing.

11. The device of claim 10, wherein the second housing includes a fluid flow path having a distal end that is in fluid communication with a lumen of the cutting assembly and a proximal end that has a conduit configured to be coupled to another device to move fluids to and from the surgical site.

12. The device of claim 11, wherein the fluid flow path extends adjacent to at least a portion of the driver component such that fluid traveling through the fluid flow path helps cool the driver components during operation.

13. The device of claim 10, wherein the control panel extends away from the central longitudinal axis at an angle that is acute with respect to the central longitudinal axis at a distal end of the second housing.

14. The device of claim 10, wherein the control panel includes one or more buttons for switching between multiple functions of the driver components.

15. The device of claim 10, wherein a proximal end of the first housing is disposed outside of the lumen of the second housing when the first housing is mated to the second housing.

16. A method of cutting tissue, comprising:
operating a surgical cutting device to cut tissue at a surgical site, the surgical cutting device having a first housing and a second housing, the second housing having a motor disposed therein, the first and second housings being removably coupled to one another, the first housing having a first shaft and a second shaft extending distally therefrom, each of the first shaft and the second shaft having a lumen formed therein and a cutting tool associated therewith, the lumens of the first and second shafts being in fluid communication with the cutting tool, with the first shaft having one or more ports thereon, the one or more ports being in fluid communication with the lumens of the first and second shafts, and a fluid flow path extending through the first housing and being in fluid communication with the lumens of the first shafts via the one or more ports;
passing fluid through the one or more ports at a location that is distal to a proximal-most end of the first shaft;
applying a suction force through the fluid flow path to move fluid and tissue away from the surgical site and toward a proximal end of the cutting device such that the passage of fluid flows from the surgical site through the lumens of the first and second shafts and passes through the one or more ports to the fluid flow path located adjacent to the motor enclosed within the second housing to cool the motor; and
detaching the first housing from the second housing.

17. The method of claim 16, further comprising cleaning and sterilizing the second housing for reuse.

18. The method of claim 16, wherein applying a suction force through the fluid flow path comprises coupling a vacuum source to a conduit of the surgical cutting device, the conduit being in fluid communication with the fluid flow path to pass fluid therethrough.

19. The method of claim 18, wherein the suction force is selectively applied by contacting a control panel disposed outside of the lumen of the first housing when the first housing is mated to the second housing.

20. The method of claim 19, wherein contacting the control panel further comprises entering a user input by applying a force to a surface of the first housing to regulate a function of the surgical cutting device.

\* \* \* \* \*